(12) United States Patent
Ferree et al.

(10) Patent No.: US 10,130,810 B2
(45) Date of Patent: *Nov. 20, 2018

(54) TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME

(71) Applicant: Neurometrix, Inc., Waltham, MA (US)

(72) Inventors: Thomas Ferree, Waltham, MA (US); Xuan Kong, Acton, MA (US); Andres Aguirre, Belmont, MA (US); Michael Williams, Melrose, MA (US); Shai N. Gozani, Brookline, MA (US)

(73) Assignee: Neurometrix, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/824,351

(22) Filed: Nov. 28, 2017

(65) Prior Publication Data

US 2018/0140834 A1     May 24, 2018

Related U.S. Application Data

(63) Continuation of application No. 14/269,887, filed on May 5, 2014, now Pat. No. 9,827,420, which is a
(Continued)

(51) Int. Cl.
*A61N 1/00* (2006.01)
*A61N 1/36* (2006.01)
(Continued)

(52) U.S. Cl.
CPC .......... *A61N 1/36021* (2013.01); *A61N 1/08* (2013.01); *G06F 3/015* (2013.01); *G06F 3/017* (2013.01);
(Continued)

(58) Field of Classification Search
CPC .............................. A61N 1/36021; A61N 1/08
(Continued)

(56) References Cited

U.S. PATENT DOCUMENTS

| 4,503,863 A | 3/1985 | Katims |
| 4,605,010 A | 8/1986 | McEwen |

(Continued)

FOREIGN PATENT DOCUMENTS

| CN | 1919139 | 2/2007 |
| CN | 101626804 | 1/2010 |

(Continued)

OTHER PUBLICATIONS

Ancoli-Israel, S. et al., The Role of Actigraphy in the Study of Sleep and Circadian Rhythms, Sleep, 2003, 26(3), p. 342-392.
(Continued)

*Primary Examiner* — Nadia A Mahmood
(74) *Attorney, Agent, or Firm* — Pandiscio & Pandiscio

(57) ABSTRACT

Apparatus for transcutaneous electrical nerve stimulation in a user, the apparatus comprising:
a housing;
stimulation means carried by the housing for electrically stimulating at least one nerve;
a pair of electrodes releasably mounted to the housing and connectable to the stimulation means for electrical stimulation of the at least one nerve;
monitoring means for monitoring user gesture, electrode-skin contact integrity and transient motion;
analysis means for analyzing the output of the monitoring means for determining user gesture, electrode-skin contact integrity and transient motion; and
control means for controlling the output of the stimulation means in response to the determined user gesture, electrode-skin contact integrity and transient motion.

28 Claims, 9 Drawing Sheets

Related U.S. Application Data continuation-in-part of application No. 14/230,648, filed on Mar. 31, 2014, now Pat. No. 9,474,898, said application No. 14/267,887 is a continuation-in-part of application No. 14/253,628, filed on Apr. 15, 2014.

(60) Provisional application No. 61/806,481, filed on Mar. 29, 2013, provisional application No. 61/811,864, filed on Apr. 15, 2013, provisional application No. 61/819,159, filed on May 3, 2013, provisional application No. 61/858,150, filed on Jul. 25, 2013.

(51) Int. Cl.
*A61N 1/08* (2006.01)
*G06F 3/01* (2006.01)
*A61B 5/11* (2006.01)
*A61N 1/04* (2006.01)

(52) U.S. Cl.
CPC ......... *A61B 5/11* (2013.01); *A61B 2560/0276* (2013.01); *A61B 2562/0219* (2013.01); *A61N 1/0456* (2013.01); *A61N 1/0492* (2013.01); *A61N 2001/083* (2013.01)

(58) Field of Classification Search
USPC .............................................. 607/40, 46, 47
See application file for complete search history.

(56) References Cited

U.S. PATENT DOCUMENTS

| | | |
|---|---|---|
| 4,738,250 A | 4/1988 | Fulkerson et al. |
| 5,063,929 A | 11/1991 | Bartelt et al. |
| 5,169,384 A | 12/1992 | Bosniak et al. |
| 5,350,414 A | 9/1994 | Kolen |
| 5,487,759 A | 1/1996 | Bastyr et al. |
| 5,562,718 A | 10/1996 | Palermo |
| 5,806,522 A | 9/1998 | Katims |
| 5,948,000 A | 9/1999 | Larsen et al. |
| 6,161,044 A | 12/2000 | Silverstone |
| 6,266,558 B1 | 7/2001 | Gozani et al. |
| 6,430,450 B1 | 8/2002 | Bach-y-Rita et al. |
| 6,456,884 B1 | 9/2002 | Kenney |
| 6,662,051 B1 | 12/2003 | Eraker et al. |
| 7,668,598 B2 | 2/2010 | Herregraven et al. |
| 7,720,548 B2 | 5/2010 | King |
| 7,725,193 B1 | 5/2010 | Chu |
| 8,108,049 B2 | 1/2012 | King |
| 8,121,702 B2 | 2/2012 | King |
| 8,131,374 B2 | 3/2012 | Moore et al. |
| 8,421,642 B1 | 4/2013 | McIntosh et al. |
| 8,825,175 B2 | 9/2014 | King |
| 8,862,238 B2 | 10/2014 | Rahimi et al. |
| 8,948,876 B2 | 2/2015 | Gozani et al. |
| 9,168,375 B2 | 10/2015 | Rahimi et al. |
| 2002/0010497 A1 | 1/2002 | Merfeld et al. |
| 2003/0023192 A1 | 1/2003 | Foxlin |
| 2003/0074037 A1 | 4/2003 | Moore et al. |
| 2003/0114892 A1 | 6/2003 | Nathan et al. |
| 2003/0208246 A1 | 11/2003 | Kotlik et al. |
| 2005/0059903 A1 | 3/2005 | Izumi |
| 2005/0080463 A1 | 4/2005 | Stahmann et al. |
| 2006/0052788 A1 | 3/2006 | Thelen et al. |
| 2006/0085049 A1 | 4/2006 | Cory et al. |
| 2006/0095088 A1 | 5/2006 | De Ridder |
| 2006/0173507 A1 | 8/2006 | Mrva et al. |
| 2006/0190057 A1 | 8/2006 | Reese |
| 2007/0060922 A1 | 3/2007 | Dreyfuss |
| 2007/0276449 A1 | 11/2007 | Gunter et al. |
| 2008/0077192 A1 | 3/2008 | Harry et al. |
| 2008/0146980 A1 | 6/2008 | Rousso et al. |
| 2008/0147146 A1 | 6/2008 | Wahlgren et al. |
| 2008/0312709 A1 | 12/2008 | Volpe et al. |
| 2009/0030476 A1 | 1/2009 | Hargrove |
| 2009/0112214 A1 | 4/2009 | Philippon et al. |
| 2009/0131993 A1 | 5/2009 | Rousso et al. |
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1 | 12/2009 | Tyler et al. |
| 2010/0004715 A1 | 1/2010 | Fahey |
| 2010/0042180 A1 | 2/2010 | Mueller et al. |
| 2010/0057149 A1 | 3/2010 | Fahey |
| 2010/0087903 A1 | 4/2010 | Van Herk et al. |
| 2010/0094103 A1 | 4/2010 | Kaplan et al. |
| 2010/0114257 A1 | 5/2010 | Torgerson |
| 2010/0131028 A1 | 5/2010 | Hsu et al. |
| 2010/0198124 A1 | 8/2010 | Bhugra |
| 2010/0217349 A1 | 8/2010 | Fahey |
| 2010/0241464 A1 | 9/2010 | Amigo et al. |
| 2011/0066209 A1 | 3/2011 | Bodlaender et al. |
| 2011/0224665 A1 | 9/2011 | Crosby et al. |
| 2011/0257468 A1 | 10/2011 | Oser et al. |
| 2011/0264171 A1 | 10/2011 | Torgerson |
| 2011/0276107 A1 | 11/2011 | Simon et al. |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2013/0096641 A1 | 4/2013 | Strother et al. |
| 2013/0158627 A1 | 6/2013 | Gozani et al. |
| 2014/0039450 A1 | 2/2014 | Green et al. |
| 2014/0107729 A1 | 4/2014 | Sumners et al. |
| 2014/0163444 A1 | 6/2014 | Ingvarsson et al. |
| 2014/0276549 A1 | 9/2014 | Osorio |
| 2014/0296934 A1 | 10/2014 | Gozani et al. |
| 2014/0296935 A1 | 10/2014 | Ferree et al. |
| 2014/0309709 A1 | 10/2014 | Gozani et al. |
| 2014/0336730 A1 | 11/2014 | Simon et al. |
| 2015/0174402 A1 | 6/2015 | Thomas et al. |
| 2015/0321000 A1 | 11/2015 | Rosenbluth et al. |
| 2015/0335288 A1 | 11/2015 | Toth et al. |

FOREIGN PATENT DOCUMENTS

| | | |
|---|---|---|
| CN | 102355847 | 2/2012 |
| CN | 102740919 | 10/2012 |
| DE | 102010052710 | 5/2012 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2005-81068 | 3/2005 |
| JP | 2006-68300 | 3/2006 |
| JP | 418546 | 9/2008 |
| WO | WO 97/42999 | 11/1997 |
| WO | WO 99/64105 | 12/1999 |
| WO | WO 2003/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2011/075179 | 6/2011 |
| WO | WO 2011/137193 | 11/2011 |
| WO | WO 2012/116407 | 9/2012 |

OTHER PUBLICATIONS

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy. American Journal of Physical Medicine & Rehabilitation, 2004, vol. 83(8): 584-591.

(56) References Cited

OTHER PUBLICATIONS

Chandran P et al., Development of opioid tolerance with repeated transcutaneous electrical nerve stimulation administration, Pain, 2003, vol. 102: 195-201.
Chen CC et al., A comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.
Chen CC et al., an investigation into the effects of frequency-modulated transcutaneous electrical nerve stimulation (TENS) on experimentally-induced pressure pain in healthy human participants, The Journal of Pain, 2009, vol. 10(10): 1029-1037.
Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.
Chen CC et al., Does the pulse frequency of transcutaneous electrical nerve stimulation (TENS) influence hypoalgesia? A systematic review of studies using experimantal pain and healthy human participants, Physiotherapy, 2008, vol. 94. 11-20.
Claydon LS et al., Dose-specific effects of transcutaneous electrical nerve stimulation on experimental pain, Clinical Journal of Pain, 2011, Vol, 27(7): 635-647.
Cole, R.J. et al., Automatic Sleep/Wake Identification From Wrist Activity, Sleep, 1992, 15(5), p. 461-469.
Cruccu G. et al., EFNS guidelines on neurostimulation therapy for neuropathic pain, European Journal of Neurology, 2007, vol. 14: 952-970.
Davies HTO et al., Diminishing returns or appropriate treatment strategy?—an analysis of short-term outcomes after pain clinic treatment, Pain, 1997, vol. 70: 203-208.
Desantana JM et al., Effectiveness of transcutaneous electrical nerve stimulation for treatment of hyperalgesia and pain, Curr Rheumatol Rep. 2008, vol. 10(6): 492-499.
Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.
Fary RE et al., Monophasic electrical stimulation produces high rates of adverse skin reactions in healthy subjects, Physiotherapy Theory and Practice, 2011, vol. 27(3): 246-251.
Fishbain, David A. et al. Does Fain Mediate the Pain interference with Sleep Problem in Chronic Pain? Findings from Studies for Management of Diabetic Peripheral Neuropathic Pain with Duloxetine, Journal of Pain Symptom Management, Dec. 2008;36(6):639-647.
Fishbain, David A. et al., Transcutaneous Electrical Nerve Stimulation (TENS) Treatment Outcome in Long-Term Users, The Clinical Journal of Pain, Sep. 1996;12(3):201-214.
Food and Drug Administration, Draft Guidance for Industry and Staff: Class II Special Controls Guidance Document: Transcutaneous Electrical Nerve Stimulator for Pain Relief, Apr. 5, 2010.
Garrison DW et al., Decreased activity of spontaneous and noxiously evoked dorsal horn cells during transcutaneous electrical nerve stimulation (TENS), Pain, 1994, vol. 58: 309-315.
Gilron, I. et al., Chronobiological Characteristics of Neuropathic Pain: Clinical Predictors of Diurnal Pain Rhythmicity, The Clinical Journal of Pain, 2013.
Hori, T. et al., Skin Potential Activities and Their Regional Differences During Normal Sleep in Humans, The Japanese Journal of Physiology, 1970, vol. 20, p. 657-671.
Jelinek HF et al., Electric pulse frequency and magnitude of perceived sensation during electrocutaneous forearm stimulation, Arch Phys Med Rehabil, 2010, vol. 91: 1372-1382.
Jin DM et al., Effect of transcutaneous electrical nerve stimulation: on symptomatic diabetic peripheral neuropathy: a meta-analysis of randomized controlled trials, Diabetes Research and Clinical Practice, 2010, vol. 89: 10-15.

Johnson MI et al., Analgesic effects of different frequencies of transcutaneous electrical nerve stimulation on cold-induced pain in normal subjects, Pain, 1989, vol. 39: 231-236.
Johnson MI et al., Transcutaneous Electrical Nerve Stimulation (TENS) and Tens-like devices: do they provide pain relief?, Pain Reviews, 2001, vol. 8: 7-44.
Johnson MI et al., Transcutaneous electrical nerve stimulation for the management of painful conditions: focus on neuropathic pain, Expert Review of Neurotherapeutics, 2011, vol. 11(5): 735-753.
Johnson, M.I. et al., An in-depth study of long-term users of transcutaneous electrical nerve stimulation (TENS). Implications for clinical use of TENS. Pain. Mar. 1991;44(3):221-229.
Kaczmarek, Kurt A. et al.. Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control; University of Belgrade. 2008;18(2):35-45.
Koumans, A. J. R. et al., Electrodermal Levels and Fluctuations During Normal Sleep, Psychophysiology, 1968, 5(3), p. 300-306.
Kripke, D.F. et al., Wrist Actigraphic Scoring for Sleep Laboratory Patients: Algorithm Development, Journal of Sleep Research, 2010, 19(4), p. 612-619.
Law PPW et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lykken, D.T., Properties of Electrodes Used in Electrodermal Measurement, J. Comp. Physiol. Psychol. Oct. 1959;52:629-634.
Lykken, D.T., Square-Wave Analysis of Skin Impedance. Psychophysiology. Sep. 1970;7(2):262-275.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Oosterhof, Jan et al., Outcome of transcutaneous electrical nerve stimulation in chronic pain: short-term results of a double-blind, randomised, placebo-controlled trial. J. Headache Pain. Sep. 2006;7(4):196-205.
Oosterhof, Jan et al., The long-term outcome of transcutaneous electrical nerve stimulation in the treatment for patients with chronic pain: a randomized, placebo-controlled trial. Pain Pract. Sep. 2012;12(7):513-522.
Pantaleao Ma et al., Adjusting pulse amplitude during transcutaneous electrical nerve stimulation (TENS) application produces greater hypoalgesia, The Journal of Pain, 2011, vol. 12(5): 581-590.
Paquet, J. et al., Wake Detection Capacity of Actigraphy During Sleep, Sleep, 2007, 30(10), p. 1362-1369.
Pieber K et al., Electrotherapy for the treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6. p. 79-92.

(56) References Cited

OTHER PUBLICATIONS

Scherder, E. J. A. et al., Transcutaneous Electrical Nerve Stimulation (TENS) improves the Rest-Activity Rhythm in Midstage Alzheimer's Disease, Behavioral Brain Research, 1999, vol. 101, p. 105-107.

Tryon, W. W., Issues of Validity in Actigraphic Sleep Assessment, Sleep, 2004, 27(1), p. 158-165.

Tsai, Y. et al., Impact of Subjective Sleep Quality on Glycemic Control in Type 2 Diabetes Mellitus, Family Practice, 2012, vol. 29, p. 30-35.

Van Boxtel, A., Skin resistance during square-wave electrical pulses of 1 to 10 mA. Med. Biol, Eng. Comput, Nov. 1977;15(6):679-687.

Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.

Webster, J. B. et al., An Activity-Based Sleep Monitor System for Ambulatory Use, Sleep, 1982, 5(4), p. 389-399.

Zelman, D. C. et al., Sleep Impairment in Patients With Painful Diabetic Peripheral Neuropathy, The Clinical Journal of Pain, 2006, 22(8), p. 681-685.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

Bonnet, M, et al., Recording and Scoring Leg Movements, Sleep, 1993, vol. 16, No. 8, p. 748-759.

Boyle, J. et al., Randomized, Placebo-Controlled Comparison of Amitriptyline, Duloxeline, and Pregabalin in Patients With Chronic Diabetic Peripheral Neuropathic Pain, Diabetes Care, 2012, vol. 35, p. 2451-2458.

Kovacevic-Ristanovic, R, et al., Nonpharmacologic Treatment of Periodic Leg Movements in Sleep, Arch. Phys. Med. Rehabil., 1991, vol. 72, p. 385-389.

Lopes, L. et al., Restless Legs Syndrome and Quality of Sleep in Type 2 Diabetes, Diabetes Care, 2005, vol. 28, No. 11, p. 2633-2636.

Nightingale, S., The neuropathic pain market. Nature Reviews, 2012, vol. 11, p. 101-102.

Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME

REFERENCE TO PENDING PRIOR PATENT APPLICATIONS

This patent application is a continuation of pending prior U.S. patent application Ser. No. 14/269,887, filed May 5, 2014 by Neurometrix, Inc. for TRANSCUTANEOUS ELECTRICAL NERVE STIMULATOR WITH USER GESTURE DETECTOR AND ELECTRODE-SKIN CONTACT DETECTOR, WITH TRANSIENT MOTION DETECTOR FOR INCREASING THE ACCURACY OF THE SAME, which in turn:

(i) is a continuation-in-part of prior U.S. patent application Ser. No. 14/230,648, filed Mar. 31, 2014 by Neurometrix, Inc. and Shai Gozani et al. for DETECTING CUTANEOUS ELECTRODE PEELING USING ELECTRODE-SKIN IMPEDANCE, which claims benefit of prior U.S. Provisional Patent Application Ser. No. 61/806,481, filed Mar. 29, 2013 by Shai Gozani for DETECTING ELECTRODE PEELING BY RELATIVE CHANGES IN SKIN-ELECTRODE IMPEDANCE;

(ii) is a continuation-in-part of pending prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE, which claims benefit of prior U.S. Provisional Patent Application Ser. No. 61/811,864, filed Apr. 15, 2013 by Shai Gozani for TRANSCUTANEOUS ELECTRICAL NERVE STIMULATOR WITH AUTOMATIC DETECTION OF PATIENT SLEEP-WAKE STATE;

(iii) claims benefit of prior U.S. Provisional Patent Application Ser. No. 61/819,159, filed May 3, 2013 by Neurometrix, Inc. and Thomas Ferree et al. for TAP DETECTOR WITH HIGH SENSITIVITY AND SPECIFICITY FOR A WEARABLE TRANSCUTANEOUS ELECTRICAL NERVE STIMULATOR; and (iv) claims benefit of prior U.S. Provisional Patent Application Ser. No. 61/858,150, filed Jul. 25, 2013 by Neurometrix, Inc. and Andres Aguirre et al. for MOVEMENT REGULATED TRIP CONDITIONS IN A WEARABLE TRANSCUTANEOUS ELECTRICAL NERVE STIMULATOR.

The seven (7) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a patient via electrodes to provide symptomatic relief of chronic pain, and more particularly to the provision of a user gesture detector and an electrode-skin contact detector in a body-worn TENS device.

BACKGROUND OF THE INVENTION

Transcutaneous electrical nerve stimulation (TENS) devices provide pain relief by electrically stimulating sensory nerves. In general, TENS devices comprise electrodes applied to the skin of a user, and leads or wires connecting each electrode to a main unit. The main unit comprises stimulation circuitry (sometimes referred to herein as the stimulator) and a user interface. The electrodes are placed on the skin of the user within, adjacent to, or proximal to, the area of pain. For conventional TENS devices, the main unit (housing the stimulator and user interface) is typically in a form of a handheld unit that is physically separated from the electrodes. Lead wires, which may be as long as 3 feet, typically connect the electrodes and the handheld unit. Users interact with the TENS device by pressing buttons on the handheld unit and gain feedback from a visual display on the handheld unit.

In users with chronic pain, there is often a need for the TENS device to be worn near continuously with minimal interference to normal daily activities. In this situation, conventional TENS designs (with their long lead wires) can be too cumbersome and prone to accidental detachment of the lead wires from the handheld unit or from the electrodes, or to accidental detachment of the electrodes from the skin of the user. For example, in users with painful diabetic neuropathy, pain is felt primarily in the feet and lower legs, and long lead wires (e.g., extending from the waist to electrodes applied to the upper calf of the user) are especially prone to detachment when users are engaged in normal daily activities such as walking or climbing stairs.

Neurometrix, Inc. of Waltham, Mass. recently developed a TENS device which provides a compact one-piece design that wraps around the upper calf of the user much like a wristwatch wraps around the wrist of a user. Details of the Neurometrix TENS device are disclosed in pending prior U.S. patent application Ser. No. 13/678,221, filed Nov. 15, 2012 by Neurometrix, Inc. and Shai N. Gozani et al. for APPARATUS AND METHOD FOR RELIEVING PAIN USING TRANSCUTANEOUS ELECTRICAL NERVE STIMULATION; pending prior U.S. patent application Ser. No. 14/230,648, filed Mar. 31, 2014 by Neurometrix, Inc. and Shai Gozani et al. for DETECTING CUTANEOUS ELECTRODE PEELING USING ELECTRODE-SKIN IMPEDANCE; and pending prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE, which patent applications are hereby incorporated herein by reference. The low-profile design of the Neurometrix TENS device allows the TENS device be discreetly worn under clothes, and eliminates the aforementioned problems associated with long lead wires extending between the electrodes and the stimulator.

Inasmuch as the aforementioned Neurometrix TENS device is configured to be worn under clothing, it would be advantageous to provide means (in addition to traditional input means such as push buttons) for a user to interact with the TENS device through clothing, e.g., through gestures such as tapping, slapping, or shaking of the TENS device.

In addition to the foregoing, an important safety consideration for TENS devices is the integrity of the electrode-skin contact interface. The TENS electrodes typically utilize hydrogels to create a stable low-impedance electrode-skin interface so as to facilitate the delivery of electrical current to the user, whereby to stimulate peripheral sensory nerves and thereby suppress pain. If the portion of the electrode in contact with the skin decreases (i.e., due to "electrode peeling", wherein the electrode peels away from the skin of the user), the current density and power density will increase due to decreased electrode-skin contact area. Increased current density and power density can lead to painful TENS stimulation and, in the extreme, thermal burns. Therefore, it is also desirable to monitor the integrity of the electrode-skin interface to safeguard the user's comfort and safety.

While the electrode-skin contact area cannot be easily measured in real-time, the contact area directly affects the impedance to the stimulation current flow, i.e., a reduced electrode-skin contact area will lead to higher impedance. Thus it is desirable to monitor the impedance across the electrode-skin interface in real-time by the TENS stimulator so as to detect electrode peeling. More particularly, if the impedance exceeds a threshold, stimulation should be halted to avoid painful stimulation sensation or potential thermal burns.

Furthermore, electric circuit theory imposes a physical limit to the maximum current a stimulator can deliver to the user, based on the maximum voltage range of the stimulator:

$$[\text{Maximum Current}] = [\text{Maximum Voltage}]/[\text{Impedance}].$$

If the electrode-skin impedance becomes too high, the maximum current deliverable by the TENS stimulator may be lower than the desired therapeutic current intensity. To ensure therapeutic efficacy of the TENS device, the TENS device should measure and monitor the actual current delivered to the user in real-time. If the measured current intensity differs from the target current intensity, then stimulation should be halted.

Wearable TENS devices provide users with pain-relieving therapy while allowing those users freedom to engage in their normal daily activities. However, activities like walking, running, and stair climbing may impose challenges to the accurate detection of intended user gestures and to maintaining a consistent electrode-skin interface. More particularly, mechanical shocks associated with walking or bumping into objects may be detected and incorrectly interpreted as user-initiated control gestures. In addition, ordinary body movements can cause momentary changes in the integrity of the electrode-skin contact and may be incorrectly interpreted as problematic and permanent changes in electrode-skin contact, even though such momentary changes in the integrity of the electrode-skin contact pose no real risk to the patient. Such "false" detections of user gestures, and/or such "false" detection of electrode peeling, can unnecessarily diminish the value of a user gesture detector and/or an electrode peeling detector for a TENS device. For these reasons, it would be advantageous to provide automated means for eliminating "false" detections of user gestures and/or for eliminating "false" detection of electrode peeling in order to increase the accuracy of user gesture recognition and electrode-skin contact detection.

SUMMARY OF THE INVENTION

The present invention comprises the provision and use of a novel TENS device which comprises an electrical stimulator and electrodes designed to be placed on a user's upper calf (or other anatomical location) to provide therapeutic electrical stimulation to the user. The novel TENS device allows a tight mechanical coupling and electrical connection between the stimulator and electrodes without the need for lead wires. A user may interact with the novel TENS device through gestures such as tapping the enclosure of the device (as well as through conventional input means such as push buttons). To this end, the novel TENS device provides automated means for eliminating "false" detections of user gestures. In accordance with the present invention, the novel TENS device also monitors the integrity of the electrode-skin interface via impedance measurements and includes automated means for eliminating "false" detections of electrode peeling.

More particularly, an accelerometer incorporated in the novel TENS device allows the device to continuously monitor user gestures. In addition, the accelerometer also allows the TENS device to monitor user body movement. A key feature of the present invention is that the TENS device uses body movement information, computed from the accelerometer data, in order to improve the accuracy of user gesture recognition and to improve the accuracy of electrode-skin contact monitoring. In particular, specific body movement patterns, as measured by the accelerometer, are used to discriminate between "true" acceleration pulse events representative of intended user gestures and "false" acceleration pulse events representative of unintended user gestures in order to improve the accuracy of user gesture recognition. Specific body movement patterns, as measured by the accelerometer, are also used to discriminate between "true" electrode-skin contact degradation (representative of actual electrode peeling) and "false" electrode-skin contact degradation (representative of transient changes of electrode-skin impedance) in order to improve the accuracy of electrode-skin contact monitoring.

Inasmuch as the novel TENS device is intended to be worn for extended periods of time, another feature of the present invention is the provision of these capabilities with minimal computational demand and power consumption.

In one preferred embodiment of the invention, the accelerometer measures acceleration along one or more axes. The acceleration data are analyzed to identify acceleration signals (i.e., acceleration pulses) likely to be caused by user gestures ("pulse detection"). The acceleration data are simultaneously analyzed by a separate algorithm to identify acceleration signals caused by the transient motion associated with ordinary body movements ("transient motion detection"). In the preferred embodiment, the accelerometer data are analyzed in real-time by a microprocessor running the two aforementioned data analysis algorithms (i.e., pulse detection and transient motion detection). The preferred embodiment of the invention integrates the data analysis results from these two algorithms (i.e., pulse detection and transient motion detection) in order to discriminate between "true" acceleration pulse events representative of intended user gestures and "false" acceleration pulse events caused by ordinary body movements (i.e., transient motion).

And in a preferred embodiment of the invention, the TENS device also monitors electrode-skin contact (by measuring impedance across the electrode-skin interface) in real-time, and is configured to stop electrical stimulation if the impedance levels indicate that electrode peeling has occurred ("electrode-skin contact detection"). In a preferred embodiment of the invention, electrode-skin contact detection is integrated with the aforementioned transient motion detection in order to discriminate between "true" electrode-skin contact degradation (representative of actual electrode peeling) and "false" electrode-skin contact degradation (representative of transient changes of electrode-skin impedance caused by ordinary body movements) in order to improve the accuracy of electrode-skin contact monitoring.

In one preferred form of the invention, there is provided apparatus for transcutaneous electrical nerve stimulation in a user, the apparatus comprising:

a housing;

stimulation means carried by the housing for electrically stimulating at least one nerve;

a pair of electrodes releasably mounted to the housing and connectable to the stimulation means for electrical stimulation of the at least one nerve;

monitoring means for monitoring user gesture, electrode-skin contact integrity and transient motion;

analysis means for analyzing the output of the monitoring means for determining user gesture, electrode-skin contact integrity and transient motion; and control means for controlling the output of the stimulation means in response to the determined user gesture, electrode-skin contact integrity and transient motion.

In another preferred form of the invention, there is provided a method for controlling transcutaneous electrical nerve stimulation based on user gesture, electrode-skin contact integrity and transient motion, the method comprising the steps of:

applying a transcutaneous electrical nerve stimulation device to the user's body;

acquiring data from an accelerometer mounted to the stimulation device that measures user gesture and transient motion;

acquiring impedance data from the stimulation device that measures the electrode-skin contact integrity;

analyzing the accelerometer data to determine user gesture;

analyzing the impedance data to determine electrode-skin contact integrity; and controlling the stimulation device based on the determined user gesture and electrode-skin contact integrity.

In another preferred form of the invention, there is provided apparatus for providing transcutaneous electrical nerve stimulation in a user, said apparatus comprising:

a housing;

stimulation means within the housing for electrically stimulating at least one nerve;

monitoring means within the housing for measuring user gesture, electrode-skin contact integrity and transient motion; and control means for controlling the electrical stimulation means when the monitoring means determines that the user gesture is intentional or the electrode-skin contact integrity degrades permanently.

In another preferred form of the invention, there is provided a method for applying transcutaneous electrical nerve stimulation to a user, said method comprising:

applying stimulation means and an accelerometer to the user's body;

delivering stimulation current to the user so as to stimulate at least one nerve;

analyzing the accelerometer data to identify a user gesture and analyzing data from the stimulation means to detect changes in electrode-skin contact integrity; and modifying the stimulation means based on intentional user gesture and permanent degradation of electrode-skin contact integrity.

In another preferred form of the invention, there is provided apparatus for providing transcutaneous electrical nerve stimulation to a user, said apparatus comprising:

an electrical stimulator;

a pair of electrodes connected to said electrical stimulator;

an accelerometer mounted to at least one of said electrical stimulator and said pair of electrodes;

an acceleration pulse detector connected to said accelerometer for detecting an acceleration pulse event associated with said accelerometer;

a transient motion detector connected to said accelerometer for detecting transient motion of the user; and a controller connected to said acceleration pulse detector and said transient motion detector for controlling operation of said electrical stimulator based on the output of said acceleration pulse detector and the output of said transient motion detector.

In another preferred form of the invention, there is provided apparatus for providing transcutaneous electrical nerve stimulation to a user, said apparatus comprising:

an electrical stimulator;

a pair of electrodes connected to said electrical stimulator;

an accelerometer mounted to at least one of said electrical stimulator and said pair of electrodes;

an electrode-skin contact detector for detecting the integrity of the contact between said pair of electrodes and the user;

a transient motion detector connected to said accelerometer for detecting transient motion of the user; and a controller connected to said electrode-skin contact detector and said transient motion detector for controlling operation of said electrical stimulator based on the output of said electrode-skin contact detector and said transient motion detector.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
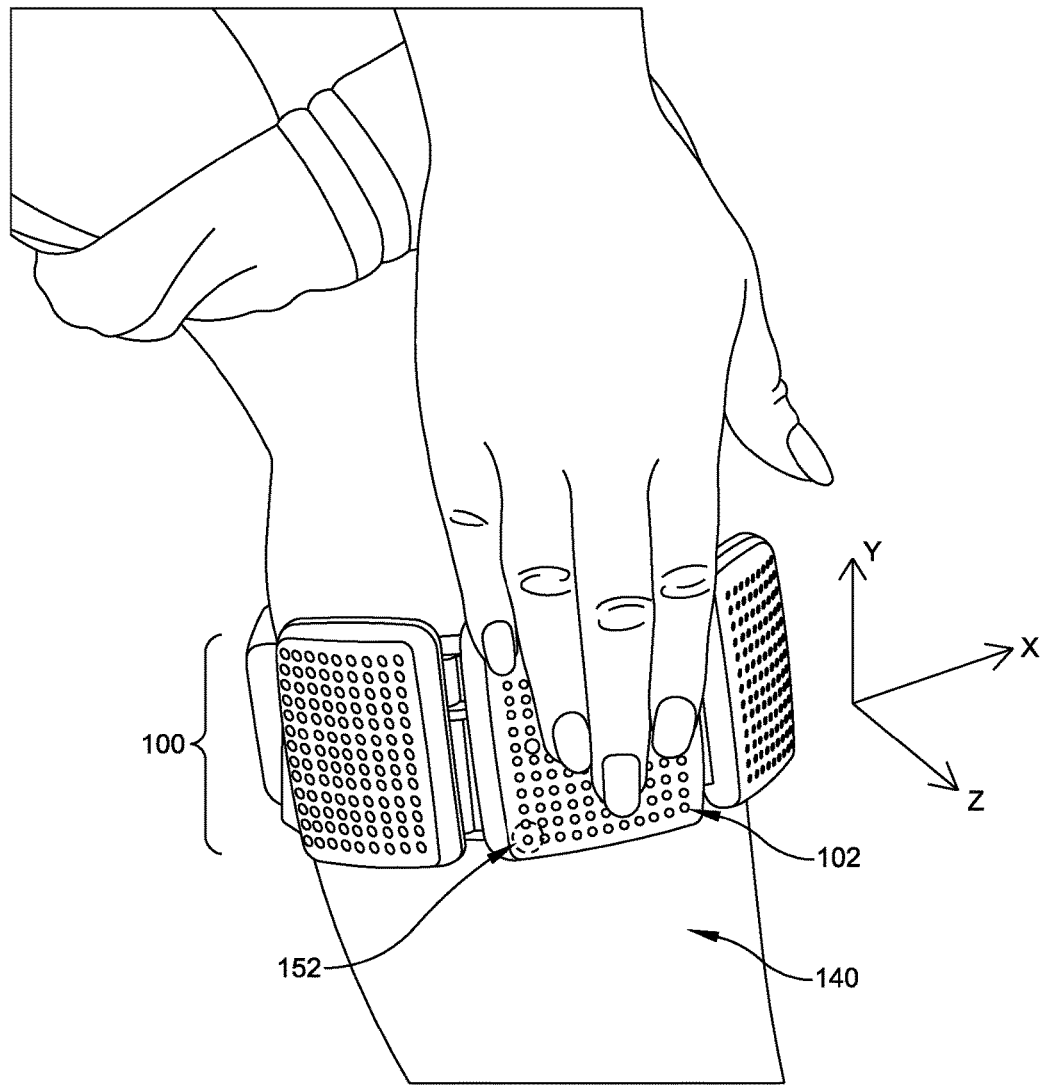
FIG. 1 is a schematic view showing a TENS device worn on the upper calf of the user, and the axes of an internal 3-axis accelerometer included in the TENS device.

FIG. 1 illustrates a novel TENS device 100 formed in accordance with the present invention, with the novel TENS device being shown worn on a user's upper calf 140. A user may wear one TENS device 100 on either leg, or wear two TENS devices, one on each leg.

Figure 1A:
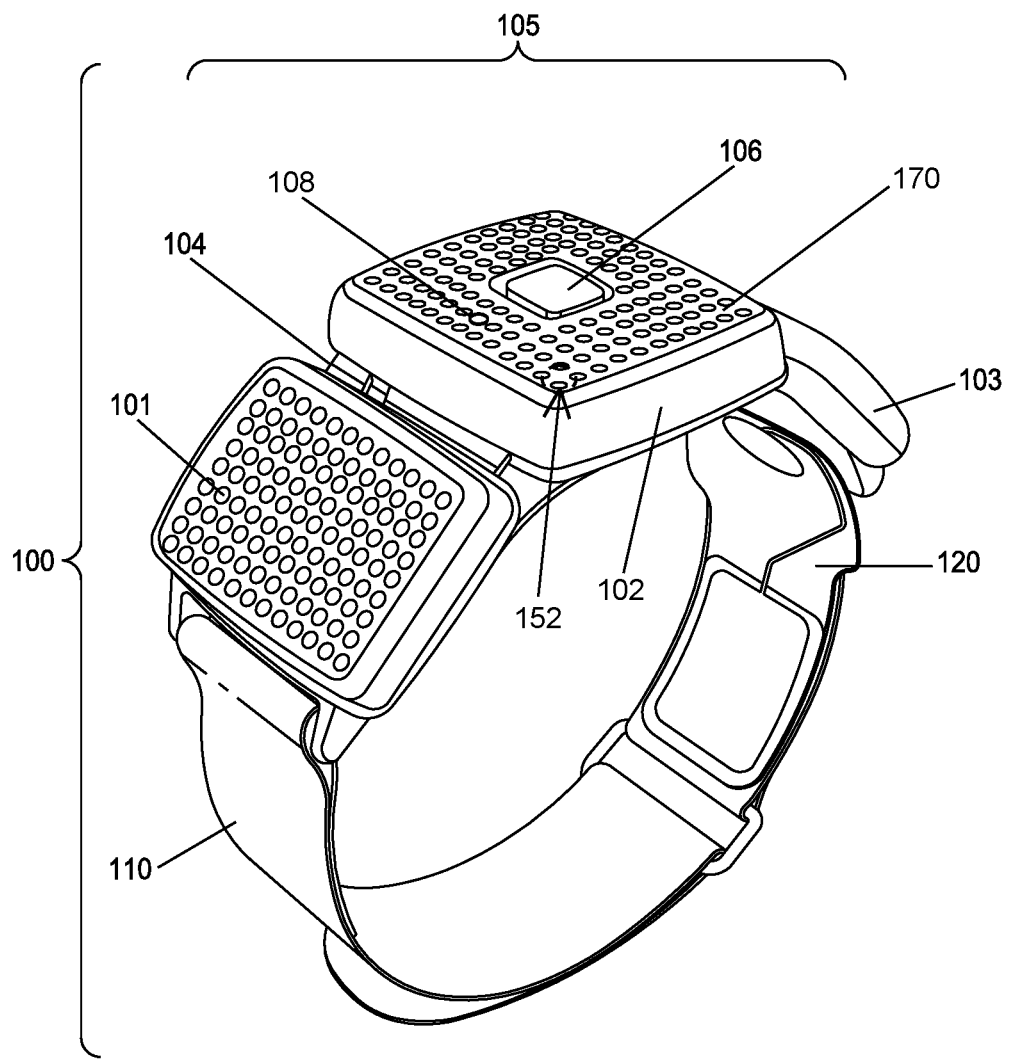
FIG. 1A is a schematic view showing the novel TENS device of FIG. 1 in greater detail.

TENS device 100 is shown in greater detail in FIG. 1A and preferably comprises three components: a stimulator 105, a strap 110, and an electrode array 120 (comprising a cathode electrode and an anode electrode appropriately connected to stimulator 105, as will hereinafter be discussed). Stimulator 105 preferably comprises three mechanically and electrically inter-connected compartments 101, 102, and 103. Compartments 101, 102, 103 are preferably inter-connected by hinge mechanisms 104 (only one of which is shown in FIG. 1A), thereby allowing TENS device 100 to conform to the curved anatomy of a user's leg. In a preferred embodiment, compartment 102 houses the TENS stimulation hardware (except for a battery) and user interface elements 106 and 108. Compartment 102 also houses an accelerometer 152, preferably in the form of a semiconductor chip accelerometer (e.g., the MMA8452Q accelerometer available from Freescale Semiconductor, Inc., Tempe, Ariz.), for detecting user gestures and user body movement, as will hereinafter be discussed. In a preferred embodiment, compartments 101 and 103 are smaller, auxiliary compartments that house a battery for powering the TENS stimulation hardware and other ancillary elements, such as a wireless interface unit (not shown) for allowing TENS device 100 to wirelessly communicate with other elements (e.g., another TENS device being worn on the other leg of the user). In another embodiment of the present invention, only one compartment 102 may be provided for housing all of the TENS stimulation hardware, battery, and other ancillary elements of the present invention without the need for side compartments 101 and 103.

Still looking now at FIG. 1A, interface element 106 preferably comprises a push button for user control of electrical stimulation, and interface element 108 comprises an LED for indicating stimulation status and providing other feedback to the user. Additional user interface elements (e.g., an LCD display, audio feedback through a beeper or voice output, haptic devices such as a vibrating motor, electrical feedback by pulsing the stimulus, etc.) may also be provided and are considered to be within the scope of the present invention.

The preferred embodiment of the present invention is designed to be worn on the upper calf 140 of the user as shown in FIG. 1. TENS device 100, comprising stimulator 105, electrode array 120, and strap 110 as shown in FIG. 1A, is secured to upper calf 140 by placing the apparatus in position and then tightening strap 110. Although the preferred embodiment of the present invention comprises placement of the TENS device on the upper calf of the user, additional anatomical locations (such as above the knee, on the lower back, and on an upper extremity) are contemplated and are also considered to be within the scope of the present invention.

Figure 1B:
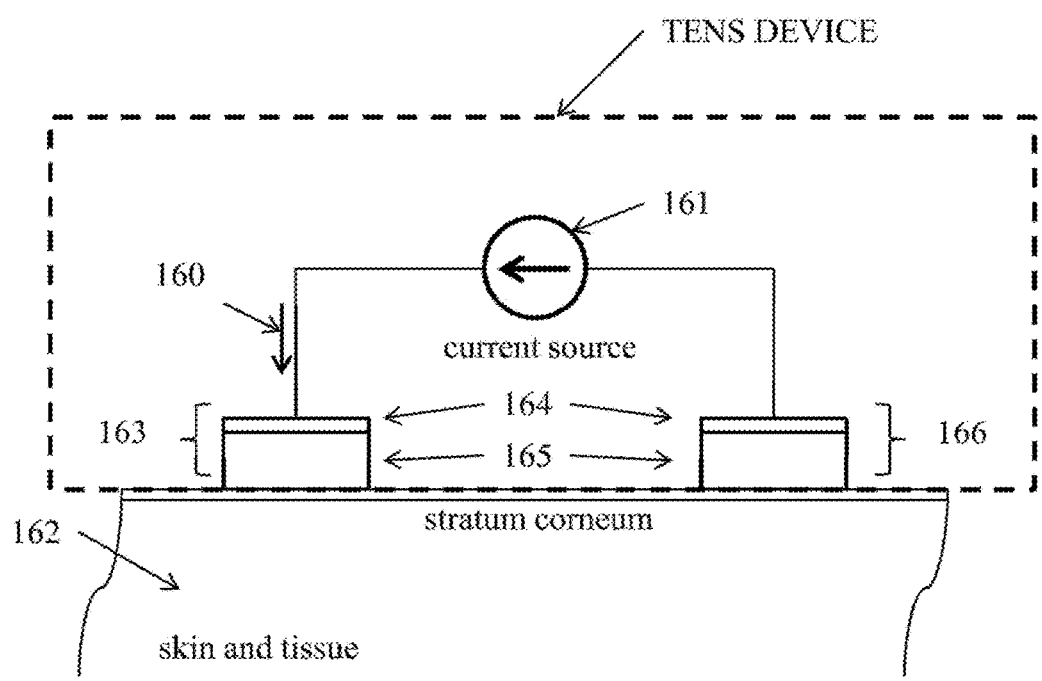
FIG. 1B is a schematic view of the electrode-skin interface of the novel TENS device shown in FIGS. 1 and 1A.

FIG. 1B is a schematic representation of the current flow between a TENS device and the user. As seen in FIG. 1B, stimulation current 160 from a controlled current source 161 flows into the user's tissue 162 via cathode electrode 163. Cathode electrode 163 consists of conductive backing (e.g., silver hatch) 164 and hydrogel 165. The current passes through the user's tissue 162 and returns to current source 161 through anode electrode 166 (anode electrode 166 also comprises a conductive backing 164 and hydrogel 165). It should be appreciated that the designation of anode and cathode electrodes is purely notational in the context of a biphasic waveform (which is the waveform preferably applied by the TENS device), i.e., when the biphasic stimulation pulse reverses its polarity in its second phase of the biphasic TENS stimulation, current will be flowing into the user's body via interface 166 and out of the user's body via interface 163.

Further details regarding the construction and use of various aspects of TENS device 100 are disclosed in (i) pending prior U.S. patent application Ser. No. 13/678,221, filed Nov. 15, 2012 by Shai N. Gozani et al. for APPARATUS AND METHOD FOR RELIEVING PAIN USING TRANSCUTANEOUS ELECTRICAL NERVE STIMULATION, which patent application is hereby incorporated herein by reference, (ii) pending prior U.S. patent application Ser. No. 14/230,648, filed Mar. 31, 2014 by Shai N. Gozani et al. for DETECTING CUTANEOUS "ELECTRODE PEELING" USING ELECTRODE-SKIN IMPEDANCE, which patent application is hereby incorporated herein by reference; and (iii) pending prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE, which patent application is hereby incorporated herein by reference.

When TENS device 100 is secured in position on the user's upper calf 140, the position and orientation of accelerometer 152 in TENS device 100 is fixed and known relative to the lower limb of the user. Tight mechanical coupling between TENS device 100 and the user's upper calf 140 allows lower limb movement to be accurately measured by accelerometer 152. Such tight mechanical coupling is established through strap 110 and the conforming shape of the device 100 accomplished by the hinge mechanisms 104.

The raw data output by accelerometer 152 reflect accelerations along each of three axes (i.e., the x-axis, the y-axis and the z-axis) sampled discretely over time. These raw data can support algorithms for detecting user gestures and user body movement, as will hereinafter be discussed. Accelerometer 152 is mounted within center compartment 102 of TENS device 100 so that one axis (i.e., the z-axis) is normal to the front face 170 (FIG. 1A) of center compartment 102. In a preferred embodiment, a single axis (i.e., the z-axis) is considered primary, and users are instructed to tap or slap the center compartment 102 of TENS device 100 along that axis (i.e., along the z-axis) in order to provide TENS device 100 with a user gesture. In other words, in a preferred embodiment, users are instructed to tap or slap front face 170 of center compartment 102 in order to provide TENS device 100 with a user gesture. Such a user gesture may then be used to control operation of TENS device 100, e.g., to turn on the device, to modify the stimulation current, to turn off the device, etc.

Figure 1C:
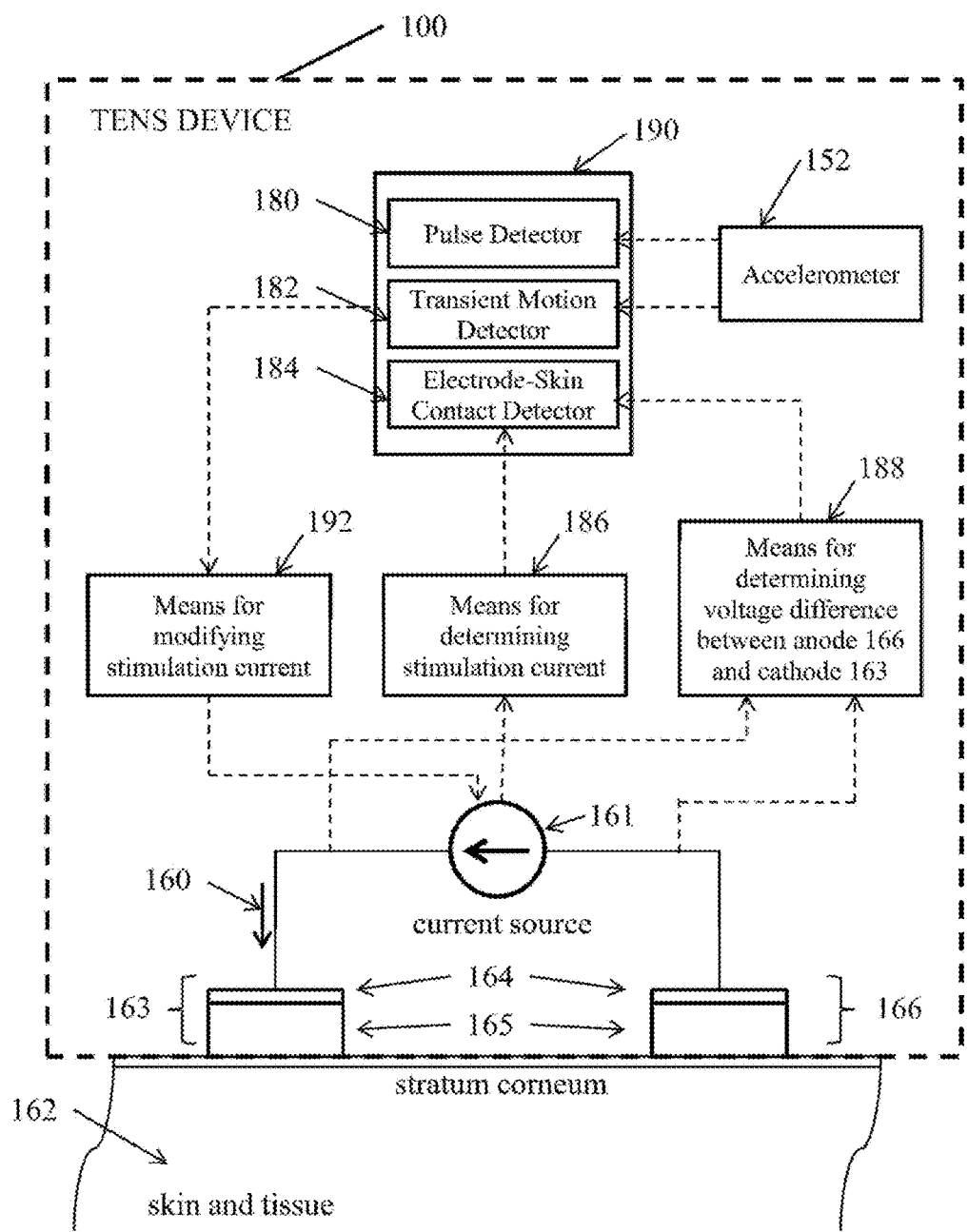
FIG. 1C is a schematic view showing further details of the novel TENS device of FIGS. 1 and 1A.

FIG. 1C shows a TENS device 100 which comprises the aforementioned accelerometer 152, a pulse detector 180 connected to accelerometer 152 for detecting acceleration pulse events as will hereinafter be discussed, and a transient motion detector 182 connected to accelerometer 152 for detecting transient motion during walking, etc. as will hereinafter be discussed. TENS device 100 also comprises an electrode-skin contact detector 184 for detecting electrode-skin contact, wherein electrode-skin contact detector 184 is connected to (i) means 186 for determining the stimulation current applied by TENS device 100 (e.g., a current sensor of the sort well known in the art), and (ii) means 188 for determining the voltage difference between the anode 163 and cathode 166 (e.g., a voltage sensor of the sort well known in the art). Pulse detector 180, transient motion detector 182 and electrode-skin contact detector 184 are preferably implemented using a microprocessor 190 of the sort well known in the art, with microprocessor 190 comprising appropriate programming to provide the functionality disclosed herein. TENS device 100 preferably also comprises means 192 for modifying or interrupting the stimulation current applied by TENS device 100 in accordance with the output of pulse detector 180, transient motion detector 182 and electrode-skin contact detector 184, e.g., a controller for controlling the controlled current source 161, wherein the controller is of the sort well known in the art, controlled by the aforementioned microprocessor so as to provide the functionality disclosed herein).

Pulse Detector

In a preferred embodiment of the present invention, the 3-axis accelerometer 152 outputs its raw acceleration measurement data at a rate of 400 Hz for each axial direction (i.e., 400 acceleration measurements per second for the x-axis direction, 400 acceleration measurements per second for the y-axis direction, and 400 acceleration measurements per second for the z-axis direction, for a total of 1200 measurements per second). In a preferred embodiment of the invention, only the acceleration data from the z-axis, $A_z(t)$, are analyzed for detection of acceleration "pulse" events, i.e., intentional gestures (e.g., taps, slaps, etc.) on the center compartment 102 by the user (the z-axis is sometimes hereinafter referred to as the "primary axis"). In another embodiment, acceleration data from each of the three axes are analyzed independently for detection of acceleration "pulse" events. In yet another embodiment, the acceleration data from all three directions are combined into instantaneous acceleration A(t), defined as $$A(t)=\sqrt{A_x(t)^2+A_y(t)^2+A_z(t)^2}$$

and this instantaneous acceleration signal is analyzed for detection of acceleration "pulse" events.

The defining characteristic of an acceleration pulse event (sometimes referred to herein as simply a "pulse"), generated by a tap or similar user gesture, is that acceleration exceeds a threshold (i.e., a positive or negative acceleration threshold), and returns below that threshold within a specified time period (i.e., a time duration threshold). The acceleration data are first high-pass filtered to remove the constant effect of gravity. In a preferred embodiment, the high-pass filter cut-off frequency is set at 2 Hz, to remove the effect of gravity while still permitting a range of other uses for the accelerometer data.

Figure 2:
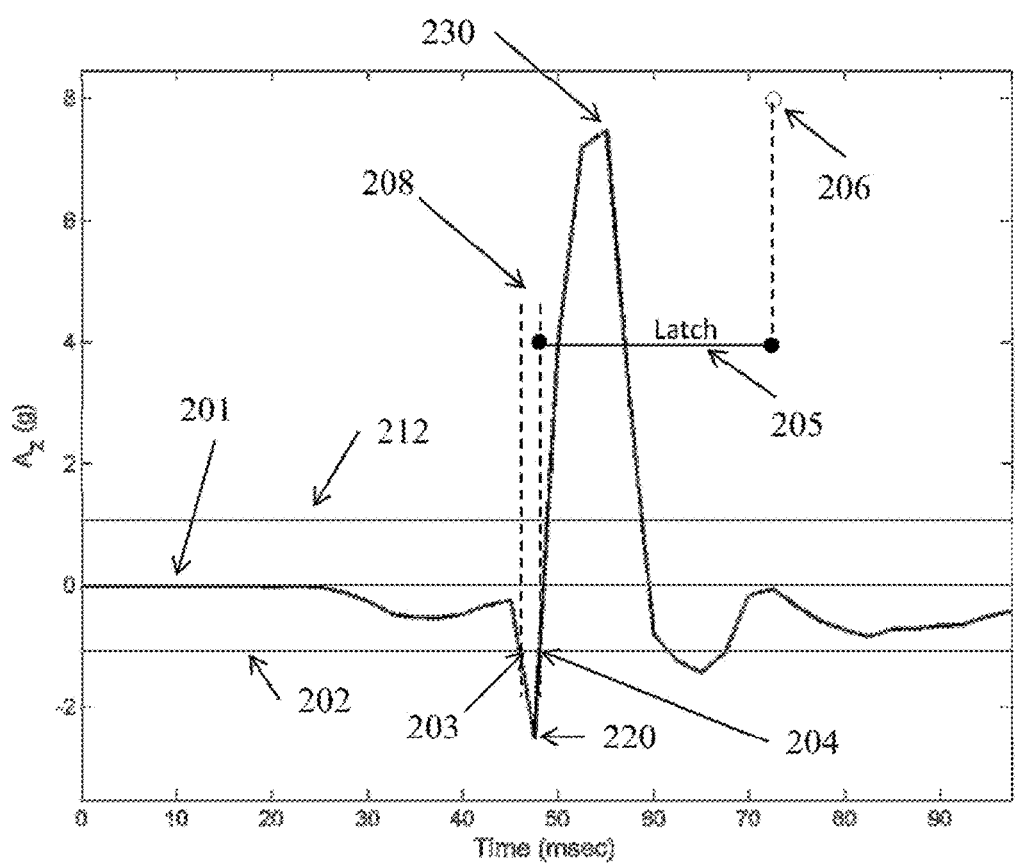
FIG. 2 is a schematic view showing an accelerometer trace reflecting a "true" pulse event initiated by an intentional user gesture.

FIG. 2 shows a sample trace 201 of $A_z(t)$ for a "true" tap event (i.e., generated by an intentional user gesture such as a tap or slap) as measured by the accelerometer. Such "true" tap events are sometimes also referred to herein as a "true" acceleration pulse event. The acceleration waveform 201 starts out near zero. When waveform 201 crosses either a positive threshold 212 or a negative threshold 202 (in this case it is the negative threshold 202), at time point 203, a timer starts. When waveform 201 crosses the same threshold 202 again, at time point 204, the timer stops. If the timer value (time difference 208 between time point 204 and time point 203) is less than a pre-determined duration threshold, then a pulse (also known as an acceleration pulse event) is considered to be detected at time point 204.

For true tap events (i.e., those reflective of an intentional user gesture), the pulse is typically largest and more stereotyped along the primary axis (i.e., along the z-axis). As a result, in a preferred embodiment, pulse detection is enabled on the specified axis only, to improve detection of true pulse events and limit "false" pulse events (i.e., those not reflective of an intentional user gesture). In another embodiment, pulse detection is carried out on all three axes. Corresponding threshold values for each axis may be different, depending upon the configuration of TENS device 100. In one embodiment, a pulse detection outcome is considered to be positive (i.e., a pulse detected) only if the pulse detection in all axis directions under consideration is positive. In another embodiment, the pulse detection outcome is considered to be positive if the pulse detection in any axis direction under consideration is positive. In yet another embodiment, the pulse detection outcome is considered to be positive if the pulse detection outcome is positive for a majority of the axes under consideration.

Depending upon the manner in which the user interacts with the TENS device, either the positive or negative peak of the pulse (i.e., the acceleration trace waveform) may be larger and cross detection threshold 202 or 212. In a preferred embodiment, crossing either positive threshold 212 or negative threshold 202, and returning within the specified time duration period, will be considered to constitute the detection of a pulse event. In other words, acceleration values between threshold 212 and threshold 202 forms a non-pulse band. A pulse event is detected when the acceleration trace waveform 201 goes outside the non-pulse band briefly for a time duration greater than zero but smaller than the specified time duration period. In one preferred embodiment, both thresholds may have the same magnitude or absolute value. In another embodiment, positive threshold 212 is larger than negative threshold 202 (in absolute value), effectively requiring that the pulse waveform have a larger positive peak in order to be recognized as a pulse event. In yet another embodiment, positive threshold 212 is set to a very large number, exceeding the largest possible measured acceleration value. Setting positive threshold 212 to such a very large number effectively causes pulse detector 180 to ignore the positive pulse peak and requires the pulse waveform to have negative polarity (i.e., a negative peak with an amplitude exceeding threshold 202) in order to constitute a pulse event.

Thus it will be seen that pulse detector 180 utilizes a pulse detection algorithm that has two main parameters: positive and negative amplitude thresholds (measured in units g, standard gravity acceleration), and a time duration threshold (measured in units msec). In a preferred embodiment, the amplitude threshold values and the time duration threshold values are fixed values which are derived experimentally, e.g., from a population study. Based on one population study, the parameters are set as follows: positive amplitude threshold: +1 g, negative amplitude threshold: −1 g, and time duration threshold: 15 msec. In another embodiment, the amplitude threshold values and the time duration threshold value are adapted to the behavior of an individual user. For example, if a stronger pulse waveform always follows a weaker pulse waveform (i.e., the weaker pulse waveform just misses the threshold value 202 and the stronger pulse waveform exceeds the threshold 202), threshold value 202 may be reduced (in absolute value) to allow pulse detector 180 to correctly recognize a weaker tap as a "true" acceleration pulse event (and hence an intentional user gesture). Similar process may be used for adaptation and differentiation of the threshold values in different axes.

Figure 3:
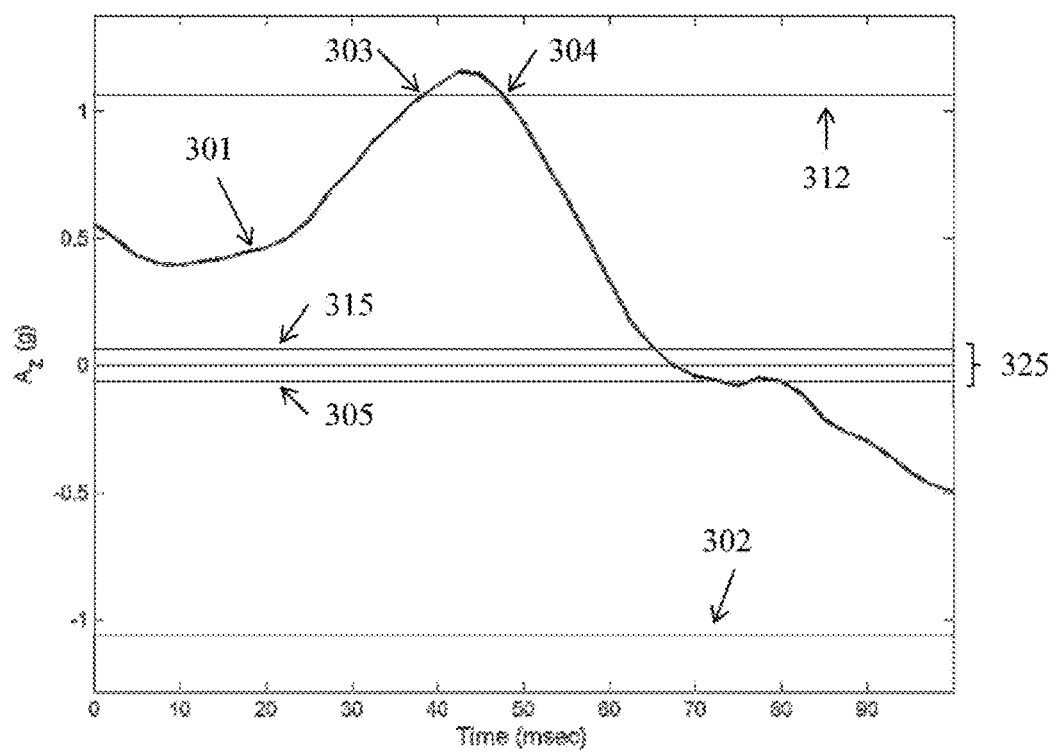
FIG. 3 is a schematic view showing an accelerometer trace reflecting a "false" pulse event initiated by body movement other than an intentional user gesture.

FIG. 3 shows an example of a "false" pulse event caused by walking. More particularly, in this example, the acceleration waveform 301 crosses the positive threshold 312 at time 303, and returns below positive threshold 312 at time 304. In contrast to a "true" acceleration pulse event like that shown in FIG. 2 (where the acceleration trace remains close to zero prior to the occurrence of a "true" acceleration pulse event), in FIG. 3 the acceleration waveform 301 prior to time 303 is consistently displaced from zero, as is typical during normal user behaviors like walking. FIG. 3 also shows a second set of thresholds (305 and 315), called transient motion thresholds, which are much smaller than the aforementioned pulse threshold 302 and 312. The acceleration values between threshold values 305 and 315 form a non-transient motion region 325. A "false" acceleration pulse event tends to have accelerations that exceed these smaller thresholds 305 and 315 (i.e., are outside the non-transient motion region 325) prior to pulse detection; this fact is used (see below) to preclude trace 301 in FIG. 3 from being classified as a "true" acceleration pulse event.

Transient Motion Detector

Figure 4:
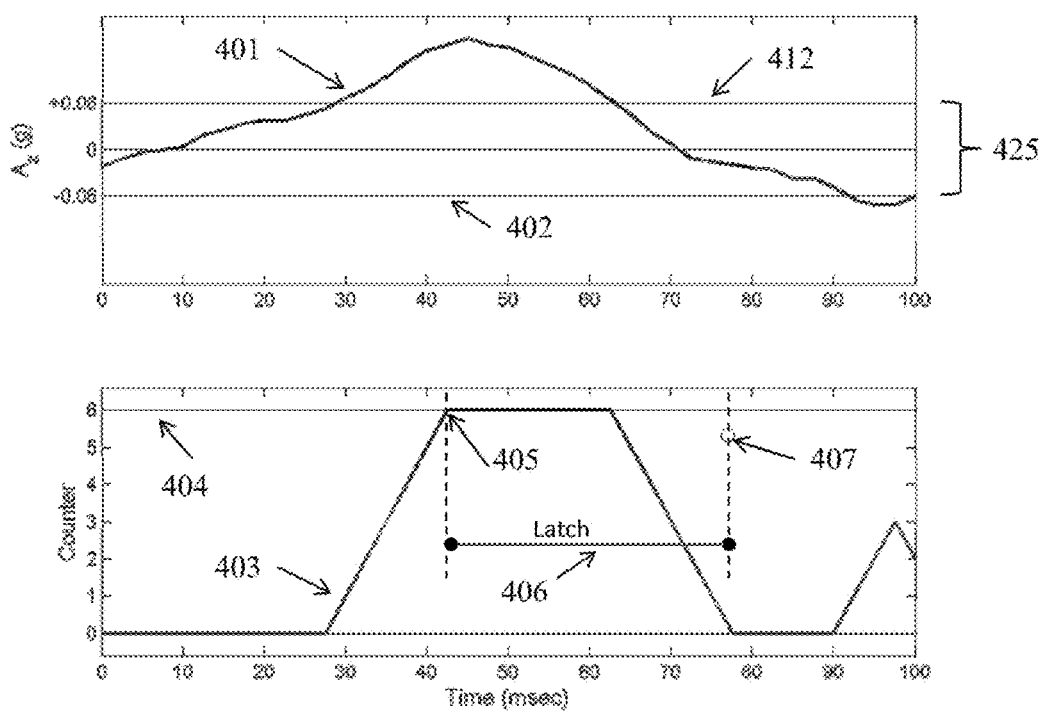
FIG. 4 is a schematic view showing an accelerometer trace reflecting transient motion associated with ordinary body movements, and an approach for identifying such transient motion.

TENS device 100 is provided with transient motion detector 182 for detecting transient motion during walking, etc. The defining feature of transient motion is that the high-pass filtered acceleration waveform exceeds some amplitude threshold, and remains above that amplitude threshold for at least some time duration. More particularly, FIG. 4 shows a segment of an acceleration waveform 401 corresponding to transient motion during walking, etc. When acceleration waveform 401 is above a transient motion threshold 412 or below a transient motion threshold 402, a counter 403 increments with each time sample taken along trace 401, otherwise counter 403 decrements. In other words, the counter 403 increments by one for each sample time if the waveform sample of the acceleration waveform 401 stays outside a non-transient motion region 425 bounded by threshold 402 and 412; otherwise the counter 403 decrements by one for each waveform sample that falls inside the non-transient motion region 425. The counter value is bounded between 0 and a specified counter threshold value 404 (e.g., a counter threshold value of 6 in FIG. 4). Any time counter value 403 is equal to threshold 404, a flag (e.g., in microprocessor 190) is set to indicate the occurrence of transient motion. With appropriate transient motion threshold 402 and 412 and counter threshold value 404, the transient motion detection algorithm utilized by transient motion detector 182 can detect body movements of the user due to walking and other normal activities. In the preferred embodiment, to maximize the detection of transient motion events, transient motion detection is enabled for all three axes (i.e., acceleration is detected, and the acceleration data utilized, for all three axes). In another embodiment, transient motion detection is only enabled for axis directions found to optimize performance of transient motion detector 182.

The transient motion detection algorithm utilized by transient motion detector 182 utilizes three main parameters: positive and negative amplitude thresholds (measured in units g), and duration threshold (measured in units msec). In a preferred embodiment, the duration threshold is converted to an equivalent discrete sample counter value for discretely sampled waveform. In a preferred embodiment, positive and negative amplitude threshold values and the counter threshold value are fixed values which are derived experimentally, e.g., from a population study. Based on one population study, the parameters are set as follows: positive amplitude threshold: +0.0625 g, negative amplitude threshold: −0.0625 g, and duration threshold: 15 msec (which corresponds to a counter threshold equal to 6 for waveforms sampled at 400 Hz). In another embodiment, positive and negative amplitude threshold values and the counter threshold value are adapted to an individual user's behavior.

Integration of Transient Motion Detector and Pulse Detector

When a user intentionally taps central compartment 102 of TENS device 100, an acceleration pulse event (or "pulse event") is created which is readily identified by the aforementioned pulse detection algorithm utilized by pulse detector 180 (i.e., pulse detector 180 is designed to have high sensitivity so as to ensure reliable detection of the acceleration pulse event). However, pulse events must correspond to actual tap events initiated by the user in order for the gesture control to be of practical value, i.e., the overall system must have high specificity. Inasmuch as transient motion such as walking can lead to "false" pulse events, these "false" pulse events must be identified and rejected without reducing the sensitivity to "true" pulse events (i.e., those reflecting intentional user gestures). Because the underlying cause of "false" pulse events is motion, the present invention detects transient motion due to walking and other normal body movements, and rejects those pulse events in close temporal proximity to transient motion. In other words, the pulse detection algorithm of pulse detector 180 must be sensitive so that it does not miss the detection of "true" pulse events caused by intentional user gestures (e.g., taps by the user on central compartment 102), but the TENS device must also be capable of discerning "false" pulse events caused by walking and other normal body movements and rejecting such "false" pulse events as being unrelated to intentional user gestures.

The temporal proximity of transient motion and acceleration pulse events provides a reliable means for discriminating between "true" acceleration pulse events corresponding to actual user gestures (e.g., taps on central compartment 102), and "false" acceleration pulse events caused by transient motion due to walking and other normal body movement. An important aspect of the present invention lies in this recognition and the determination of such temporal proximity.

Pulse events have sharp initial deflections lasting 10-20 msec, followed by decaying oscillations lasting 50-100 msec. Thus, even "true" pulse events (i.e., those reflective of an intentional user gesture) generate transient motion events immediately after the "true" pulse event. Therefore, in the preferred embodiment, transient motion events immediately following pulse events are ignored for purposes of discriminating between "true" pulse events and "false" pulse events. However, transient motion events temporally separated from pulse events are used to discriminate between "true" pulse events and "false" pulse events.

Figure 5:
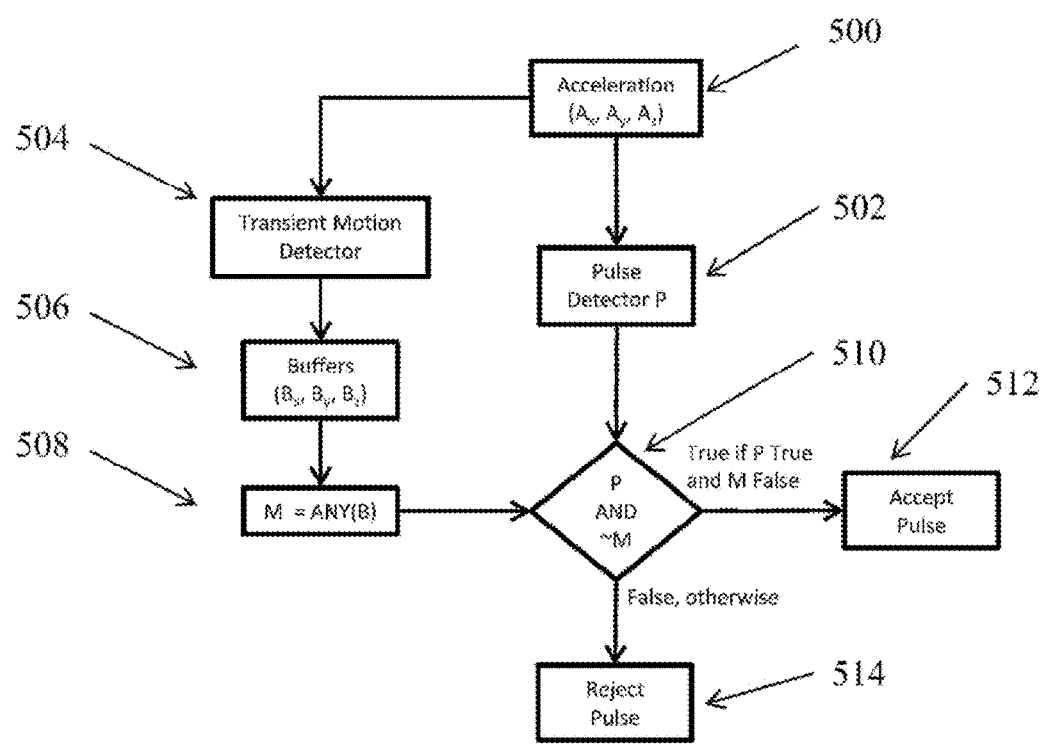
FIG. 5 is a flowchart showing how transient motion events can be used to discriminate between "true" acceleration pulse events representative of intended user gestures and "false" pulse events representative of ordinary body movements.

More particularly, FIG. 5 shows a flowchart for a preferred embodiment of the present invention. The acquired acceleration data (block 500) from each axis ($A_x(t)$, $A_y(t)$, $A_z(t)$) are processed individually by transient motion detector 182 (block 504) to detect transient motion as described above. Detected transient motion events are stored in a buffer (block 506) for each axis ($B_x$, $B_y$, $B_z$). The buffer contents are updated to include only events detected in the most recent time period (e.g., in the most recent 150 msec). If any of the buffers is "true" (i.e., reflecting a detected transient motion event), then microprocessor 190 sets a transient motion flag M to "true" (block 508); otherwise, the transient motion flag M is set to "false".

The acceleration data 500 from the primary axis direction ($A_z(t)$) are processed by pulse detector 180 (block 502). The current pulse detection result P, and a history of transient motion detection results (summarized by flag M), are analyzed by the microprocessor 190 (block 510). When a pulse is detected (i.e., pulse detect flag P is "true"), if transient motion is absent (i.e., if transient motion flag M is "false"), then microprocessor 190 accepts the pulse event as a "true" pulse event (block 512) which is reflective of an intentional user gesture, otherwise microprocessor 190 rejects the pulse event as a "false" pulse event (block 514).

The temporal proximity of transient motion and acceleration pulse events provides the means for discriminating between "true" acceleration pulse events corresponding to actual user gestures (e.g., taps on central compartment 102), and "false" acceleration pulse events caused by transient motion due to walking and other normal body movement. The duration of the buffers (block 506) sets the degree of temporal proximity required between transient motion events and acceleration pulse events when discriminating between "true" acceleration pulse events and "false" acceleration pulse events.

In the preferred embodiment, the duration of the buffers (block 506) is determined by an optimization procedure based upon data acquired from users wearing the device.

One key factor in this optimization is the following. By the laws of physics, specifically kinematics, linear displacement of an object from one relatively stationary state to another involves acceleration in one direction (initiation of movement) followed by acceleration in the opposite direction (cessation of movement). Accelerometer data from a pulse, like that in FIG. 3, shows two prominent peaks 220 and 230 consistent with this physical understanding. A sample rate of 400 Hz is fast enough to capture these peaks, but different examples of pulse waveforms have different relative peak sizes, presumably because the accelerometer samples have effectively random temporal alignments with respect to the actual physical peaks. In FIG. 2, the negative peak 220 was followed by a positive peak 230 that happened to be larger. The negative peak 220 crossed the negative threshold 202, and resulted in the detection of the pulse at time 203 based on that negative peak. Depending upon the overall shape of the pulse waveform 201 and the negative threshold 202, however, the first peak 220 may not result in pulse detection. Depending upon the size of the second peak 230 and the positive threshold 212, it may be the second peak that results in pulse detection. In such a case, even though the first peak 220 did not result in pulse detection, it may cross the transient motion detection threshold 402 (FIG. 4) and, depending up the acceleration profile and transient motion duration threshold, it may result in the detection of transient motion. In the preferred embodiment, therefore, the transient motion buffers 506 span a time interval that excludes an interval (0-50 msec) immediately preceding a detected pulse. In the preferred embodiment, these buffers include the time interval 50-150 msec before a detected pulse. Other values of these parameters have been contemplated and are considered to be within the scope of the present invention.

Electrode-Skin Contact Monitor

As discussed above, a robust electrode-skin interface is important for the effective, comfortable and safe operation of a TENS device. Therefore, the present invention includes the provision of an electrode-skin contact detector 184 for monitoring electrode-skin contact and detecting the occurrence of electrode peeling.

More particularly, the interface between the TENS electrodes and the skin of the user is electrically characterized by the measured electrode-skin impedance. The electrode-skin contact detector 184 of TENS device 100 measures the voltage across its anode and cathode terminals via means 188 in FIG. 1C. Because the hydrogel has effectively zero impedance, this is the same voltage that spans the anode and cathode electrodes. Because the electrode-skin impedance is generally much larger than the body's internal tissue impedance, dividing the anode-cathode voltage difference by the stimulation current (measured via means 186 in FIG. 1C) yields the electrode-skin impedance. Several factors influence the electrode-skin impedance, including the contact area between the skin and electrode, and the quality of the contact between the skin and the electrode gel.

Electrode-skin contact detector 184 of novel TENS device 100 monitors the electrode-skin contact integrity through electrode-skin impedance measurements. The electrode-skin contact integrity can be degraded permanently because the electrode is dislodged from its original position and loses contact with the skin (so-called electrode peeling). The electrode-skin contact integrity can also be compromised when the conductive gel on the electrode is dehydrated. When increases in the electrode-skin impedance are due to causes like these, the TENS stimulation should be stopped immediately as manual interventions are required to restore the integrity of the electrode-skin contact. If the TENS stimulation continues after the electrode-skin contact integrity has been compromised, excessive stimulation current density may result in painful sensation or thermal burn from the stimulation current. High electrode-skin impedance may also lead to so-called "compliance conditions" where the stimulation current cannot be delivered at the intended target level, resulting in a loss of TENS therapy efficacy. For these reasons, electrode-skin contact monitor 184 monitors the electrode-skin impedance (obtained by dividing the anode-cathode voltage difference by the stimulation current, where the anode-cathode voltage difference is measured via means 188 in FIG. 1C and the stimulation current is measured by means 186 in FIG. 1C).

Inasmuch as novel TENS device 100 is designed to be worn by users without any restrictions on their daily routine activity, the electrode-skin contact condition may be momentarily degraded due to physical activities such as walking or climbing stairs. If the brief degradation of the electrode-skin contact integrity is in close temporal proximity with motion, then immediate termination of the TENS stimulation may not be necessary. This is because such degradation of the electrode-skin contact integrity is likely to be momentary and the quality of the electrode-skin contact integrity will likely be restored once motion stops without any additional manual intervention.

The present invention discloses an approach (see below) for detecting momentarily degradation of the electrode-skin contact integrity. With this detection scheme, novel TENS device 100 can continue TENS stimulation during any momentary degradation of the electrode-skin contact integrity which is attributable to user activities, while still maintaining its sensitivity and fast reaction time to terminate TENS stimulation (in order to avoid the risk of painful stimulation sensation or thermal burns) where there is a permanent loss of electrode-skin contact integrity (e.g., due to electrode peeling).

Integration of Transient Motion Detector with Electrode-Skin Contact Detector

On account of the foregoing, in one preferred form of the present invention, novel TENS device 100 uses both the output of electrode-skin contact detector 184 and transient motion detector 182 to identify "true" detections of electrode peeling (in which case operation of TENS device 100 is halted) and "false" detections of electrode peeling (in which case operation of TENS device 100 is maintained).

Figure 6:
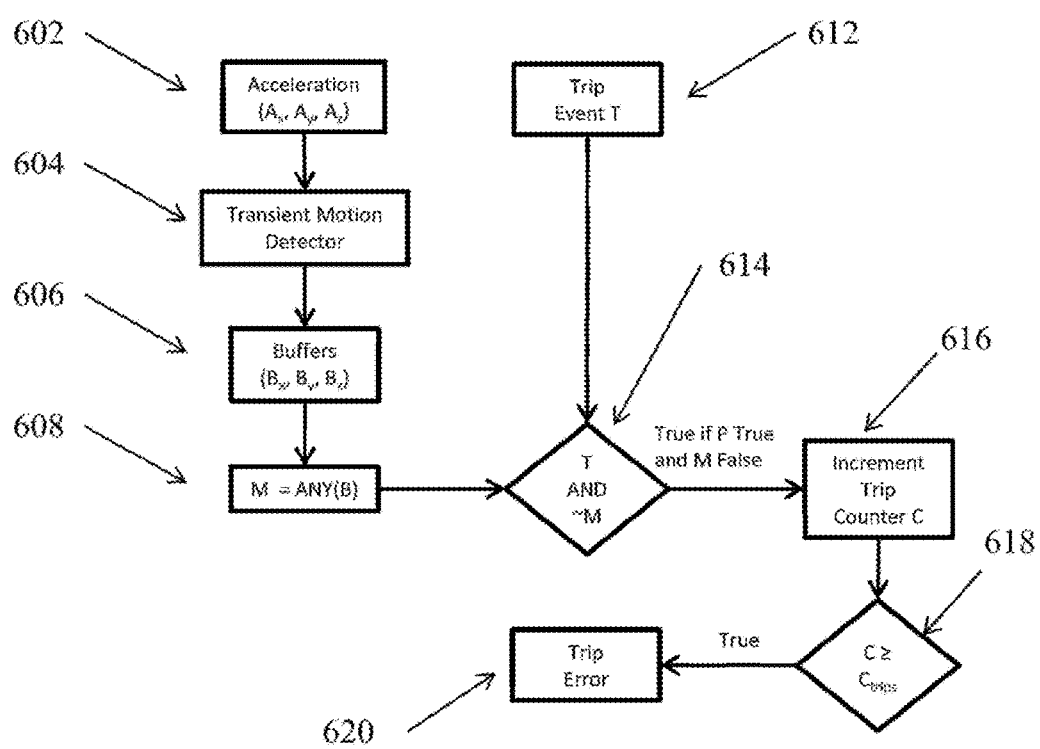
FIG. 6 is a flowchart showing how transient motion events can be used to discriminate between "true" electrode-skin contact degradation (representative of actual electrode peeling) and "false" electrode-skin contact degradation (representative of ordinary body movements).

More particularly, a preferred approach for enhanced monitoring of the electrode-skin interface is shown in FIG. 6. Acceleration data (block 602) from the three individual axes monitored by accelerometer 152 are analyzed by transient motion detector 182 (block 604). Detected transient motion events are stored in a buffer (block 606) for each axis ($B_x$, $B_y$, $B_z$). The buffer contents are updated to include only events detected in a most recent past time period (e.g., 500 msec). If any of the buffers is "true", then microprocessor 190 sets a transient motion flag M to "true"; otherwise, the flag M is set to "false" (block 608).

Electrode-skin contact detector 184 detects any "trip" condition (i.e., increased impedance) that is indicative of the degradation of the electrode-skin contact integrity due to electrode peeling (block 612). If such a "trip" condition is detected, microprocessor 190 sets a trip condition flag T to "true"; otherwise the microprocessor sets the flag to "false". Microprocessor 190 examines the status of flags M and T (block 614). If the flag T is "true" and flag M is "false", then a "trip condition" counter C is incremented by microprocessor 190 (block 616). Every time the trip condition counter C is incremented, its value is compared against a preset threshold $C_{trips}$ by microprocessor 190 (block 618). If the trip condition counter C exceeds the value of preset threshold $C_{trips}$, a permanent trip condition is identified, and microprocessor 190 will cause means 192 (FIG. 1C) to stop the stimulation current (block 620).

Duration of the buffers ($B_x$, $B_y$, $B_z$) (block 606) are derived experimentally, e.g., from a population study. In a preferred embodiment, the buffer spans a 500 msec window before the trip event, and $C_{trips}=3$, but other values have been contemplated and are within the scope of this invention. Other embodiments of this algorithm have been contemplated and are also within the scope of this invention. In one embodiment, the buffer duration and the trip counter threshold are fixed. In another embodiment, $C_{trips}$ is increased beyond 3 during transient motion events. In another embodiment, the impedance thresholds for meeting a "trip" condition are increased during transient motion events. Such increases in $C_{trips}$ or impedance thresholds may be fixed, or may be proportional to the amount of activity, e.g., the number of transient motion events in a backward-looking time window.

Modifications of the Preferred Embodiments

In the preferred embodiments described above, accelerometer 152 samples acceleration fast enough (e.g., 400 Hz) to capture fast acceleration pulse events. In addition, TENS device 100 includes a microprocessor 190 that controls overall functionality, including user inputs and feedback, stimulation, and skin-electrode contact monitoring. Microprocessor 190 also uses the output of the accelerometer to provide certain automatic controls of the device, e.g., through integration of accelerometer functions with each other and with skin-electrode contact monitoring.

In one modification of the preferred embodiments, microprocessor 190 queries the various elements of the TENS device at a slower rate (e.g., 25 Hz) than the accelerometer sampling rate (e.g., 400 Hz). This allows microprocessor 190 time for other necessary operations and conserves power. In one embodiment of this modification, accelerometer 152 latches the microprocessor "pin" (i.e., input) that reports pulse detection, as indicated in FIG. 2 by the line 205, until microprocessor 152 is able to read that pin at time 206. In this way, any pulse detected between two 25 Hz queries of the accelerometer will be reported to the microprocessor without loss. Similarly, the accelerometer latches the microprocessor "pin" (i.e., input) that reports transient motion detection, as indicated in FIG. 4 by the line 406, until the microprocessor is able to read that pin at time 407.

What is claimed is:

1. A method for controlling transcutaneous electrical nerve stimulation based on user gesture, electrode-skin contact integrity and transient motion of the user, the method comprising the steps of:
   applying a transcutaneous electrical nerve stimulation unit to the user's body;
   monitoring at least one selected from the group consisting of user gesture, electrode-skin contact integrity and transient motion of the user;
   analyzing at least one of (i) the user gesture and the transient motion to determine whether an intentional user gesture has occurred, and (ii) the
   electrode-skin contact integrity and the transient motion to determine whether a non-transient degradation of the electrode-skin contact integrity has occurred; and
   modifying operation of the stimulation unit in response to at least one of the determination of an intentional user gesture and a non-transient degradation of the electrode-skin contact integrity.

2. A method according to claim 1 wherein monitoring the electrode-skin contact integrity is accomplished with the impedance measurements by dividing the voltage difference across the outputs of the stimulation unit divided by the stimulation current of the stimulation unit.

3. A method according to claim 2 wherein a collection of said impedance values is used to quantify a change in electrode-skin contact integrity.

4. A method according to claim 3 wherein the electrode-skin contact integrity is determined to be degraded if the most recent impedance value is significantly different from a baseline impedance value.

5. A method according to claim 4 wherein the baseline impedance value is a fixed impedance value.

6. A method according to claim 4 wherein the baseline impedance value is the minimum of all electrode-skin impedance values in the collection.

7. A method according to claim 3 wherein the electrode-skin contact integrity is determined to be degraded when the ratio between the most recent electrode-skin impedance value and the baseline electrode-skin impedance value exceeds a ratio threshold.

8. A method according to claim 7 wherein the ratio threshold is 1.8.

9. A method according to claim 1 wherein monitoring user gesture is based on acceleration data in one or more axes of three-dimensional space from one or more accelerometers.

10. A method according to claim 9 wherein the static earth gravity component is removed from the acceleration data.

11. A method according to claim 1 wherein user gesture is detected when a pulse event is detected in the acceleration data.

12. A method according to claim 11 wherein a pulse event is an acceleration signal segment with amplitude exceeding a non-pulse band for a period no longer than a pulse duration threshold.

13. A method according to claim 12 wherein the non-pulse band contains zero gravity value.

14. A method according to claim 12 wherein the non-pulse band comprises a positive threshold value and a negative threshold value, and further wherein the positive threshold value and the negative threshold value are independently set.

15. A method according to claim 12 wherein the non-pulse band comprises a positive threshold value and a negative threshold value, and further wherein the pulse duration threshold is a function of the positive threshold value and negative threshold value.

16. A method according to claim 15 wherein the function is a constant function of 15 milliseconds.

17. A method according to claim 15 wherein the function is an increasing function.

18. A method according to claim 15 wherein the function is a logarithm function.

19. A method according to claim 9 wherein a transient motion caused by the body movement of the user is determined to be present if the acceleration signal stays outside a non-transient motion region for a duration of at least a transient duration threshold.

20. A method according to claim 19 wherein the non-transient band is an acceleration value range that contains a zero-gravity value.

21. A method according to claim 19 wherein the non-transient band comprises a positive threshold value and a negative threshold value, and further wherein the positive threshold value and negative threshold value of the non-transient band are independently set.

22. A method according to claim 1 wherein a user gesture is determined to be an intentional user gesture if no transient motion is in a time window prior to the pulse event.

23. A method according to claim 1 wherein the electrode-skin contact integrity degradation is determined to be a non-transient degradation if no transient motion is detected in a time window immediately prior to detection of electrode-skin contact degradation.

24. A method according to claim 23 wherein the electrode-skin contact integrity degradation is determined to be permanent if the number of occurrences of non-transient electrode-skin contact integrity degradation exceeds a threshold.

25. A method according to claim 1 wherein the stimulation unit stops electrical stimulation when a permanent degradation of the electrode-skin contact integrity is detected.

26. A method according to claim 1 wherein the stimulation unit stops electrical stimulation if an intentional user gesture is detected when stimulation is on-going.

27. A method according to claim 1 wherein the stimulation unit starts electrical stimulation if an intentional user gesture is detected when no stimulation is on-going.

28. A method for providing transcutaneous electrical nerve stimulation to a user, said method comprising:
   applying stimulation means with an accelerometer to the user's body;
   delivering stimulation current to the user to stimulate at least one nerve;
   monitoring at least one of (i) user gesture and transient motion of the user for determining whether an intentional user gesture has occurred, and (ii) electrode-skin contact integrity and transient motion of the user for determining whether non-transient degradation of the electrode-skin contact integrity has occurred; and
   modifying the electrical stimulation means when an intentional user gesture or non-transient degradation of electrode-skin contact integrity is detected.

* * * * *